United States Patent [19]

Fischer

[11] Patent Number: 4,529,546
[45] Date of Patent: Jul. 16, 1985

[54] PURIFICATION OF VITAMIN $D_3$

[75] Inventor: Martin Fischer, Ludwigshafen, Fed. Rep. of Germany

[73] Assignee: BASF Aktiengesellschaft, Fed. Rep. of Germany

[21] Appl. No.: 613,349

[22] Filed: May 23, 1984

[30] Foreign Application Priority Data

May 26, 1983 [DE] Fed. Rep. of Germany ....... 3319026

[51] Int. Cl.$^3$ ................................................. C07J 9/00
[52] U.S. Cl. ............................. 260/397.2; 260/397.25
[58] Field of Search ........................ 260/397.2, 397.25

[56] References Cited

U.S. PATENT DOCUMENTS

| | | | |
|---|---|---|---|
| 2,264,320 | 12/1941 | Linsert | 200/397.2 |
| 3,176,029 | 3/1965 | Bharucha | 260/397.2 |
| 3,334,118 | 8/1967 | Schaaf et al. | 260/397.25 |
| 3,367,950 | 2/1968 | Salwa | 260/397.25 |
| 4,263,103 | 4/1981 | Johnson et al. | 260/397.25 |
| 4,388,242 | 6/1983 | Malatesta et al. | 260/397.2 |

FOREIGN PATENT DOCUMENTS

| | | | |
|---|---|---|---|
| 370743 | 4/1932 | United Kingdom | 260/397.2 |
| 491653 | 9/1938 | United Kingdom | 260/397.2 |

OTHER PUBLICATIONS

The Vitamins, vol. III, 203, 1971.
Diels–Alder–Reaktion, H. Wollweber, Georg Thieme Verlag Stuttgart, 1972, pp. 54 to 65, 185–212.
H. Sauer, Angewandte Chemie, 1967, 79, p. 76.
The Application of Molecular Distillation, Hallo et al, Akademiai Kiado Budapest, 1971.

*Primary Examiner*—Elbert L. Roberts
*Attorney, Agent, or Firm*—Keil & Weinkauf

[57] ABSTRACT

Crude vitamin $D_3$ is purified by reaction with a dienophile followed by short-path distillation.

5 Claims, No Drawings

PURIFICATION OF VITAMIN D$_3$

The present invention relates to a process for the purification of crude vitamin D$_3$ by combining a conventional treatment with a dienophile and a short-path distillation.

When 7-dehydrocholesterol or ergosterol is irradiated and the unreacted starting material is separated off, vitamin D$_2$ resin or vitamin D$_3$ resin, which has a vitamin content of about 63%, is obtained (The Vitamins, Vol. III, page 203, 1971, W. H. Sebrell, Jr. and R. S. Harris ed.). The vitamin D content is the sum of the contents of vitamin D and provitamin D. The vitamin D resin also contains some isomers, such as tachysterol, lumisterol and ergosterol or 7-dehydrocholesterol.

There has been no lack of attempts to separate vitamin D$_2$ and vitamin D$_3$ from the by-products formed during irradiation. For example, the content of vitamin D$_3$ can be increased by forming crystalline adducts with 7-dehydrocholesterol (FR No. 1,378,121 and U.S. Pat. No. 3,367,950) or cholesterol (U.S. Pat. No. 2,264,320). Crystalline esters of vitamin D$_2$ or D$_3$, e.g. the dinitrobenzoates, can also be prepared. Such esters can be purified by recrystallization, and then hydrolyzed to give highly concentrated vitamin D preparations. Finally, crude vitamin D has also been reacted with maleic anhydride and citraconic anhydride with the object of converting the tachysterol selectively to Diels-Alder adducts, which can then be extracted with alkali (GB Nos. 370,743 and 491,653).

However, all of the conventional methods are technically very involved and entail substantial losses of the expensive vitamins, and some of them produce negligible purification effects. In particular, the purification method which employs maleic anhydride or citraconic anhydride has not become an established one because, apart from tachysterol, vitamin D$_2$ and vitamin D$_3$ also react with these dienophiles and hence undergo decomposition. Moreover, traces of acid, which can readily form from the anhydrides, catalyze the decomposition of the vitamins.

It is an object of the present invention to provide a process which permits purification of the crude vitamin D$_3$ with very little loss of vitamin activity.

We have found that this object is achieved, and that, surprisingly, a significant part of the impurities can be removed from vitamin D$_2$ or D$_3$ resin without loss of vitamin, if the crude resin is reacted with a dienophile in the presence or absence of a solvent, and the product is then subjected to a short-path distillation under reduced pressure.

Short-path distillation, also known as molecular distillation, is a method in which the material being distilled traverses a short distance in passing from a heated surface to a cooled surface; in the present case, the residence time on the heated surface should be very short, e.g. less than 10 minutes at 190° C.

Suitable apparatuses are described in, for example, The Application of Molecular Distillation by Hollo, Kurucz and Borodi, published by Akademiai Kiado, Budapest 1971. Particularly suitable apparatuses are those in which thin films are produced on the evaporator surface by means of gravity or mechanical distribution. Specific examples are falling-film evaporators with or without wipers, the distance between the heated surface and the cooled surface advantageously being no longer than the free path of the molecules under the chosen temperature and pressure conditions. As a rule, this is from a few millimeters to a few centimeters, for example less than 5, preferably from 0.3 to 3, centimeters.

Suitable dienophiles are any unsaturated compounds which readily undergo Diels-Alder addition reactions with electron-rich dienes, such as cyclopentadiene, butadiene or 9,10-dimethylanthracene, with the proviso that they do not contain any strongly acidic functional groups or any structural elements, e.g. acid chloride or anhydride groups, which can react with alcohols or water to form strong acids. Dienophiles are described in detail in, for example, H. Wollweber, Diels-Alder-Reaktionen, Georg Thieme Verlag, Stuttgart, 1972, pages 54–65 and 185–212, and in H. Sauer, Angew. Chemie 79 (1967) 76.

Accordingly, specific examples are p-benzoquinone, maleic acid N-methylimide, maleic acid N-butylimide, maleic acid N-phenylimide, esters of fumaric acid with lower aliphatic alcohols, esters of maleic acid with lower aliphatic alcohols, acrylonitrile, methacrylonitrile, 1,2-dicyanoethylene, 1,1-dicyanoethylene, esters of acrylic acid with lower aliphatic alcohols or diols, esters of methacrylic acid with lower aliphatic alcohols, esters of acetylenedicarboxylic acid with lower aliphatic alcohols, esters of propiolic acid with lower aliphatic alcohols, unsaturated sulfones, such as 1,2-diphenylsulfonylethylene, unsaturated ketones, such as 1,2-dibenzoylethylene, unsaturated nitro compounds, such as $\beta$-nitrostyrene, esters of azodicarboxylic acids with lower aliphatic alcohols, electron-deficient aromatic azo compounds, such as p,p'-dinitroazobenzene, and nitroso compounds, such as nitrosobenzene.

In order to facilitate the subsequent short-path distillation, it is advantageous to choose dienophiles which are substantially more volatile than vitamin D. Thus, residual unreacted dienophile remaining after the reaction with vitamin D resin can be distilled off before the short-path distillation of the vitamin. Particularly suitable dienophiles are methyl acrylate, ethyl acrylate, n-butyl acrylate, butanediol diacrylate, p-benzoquinone and N-methylmaleimide.

As a rule, from 0.05 to 5, preferably from 0.1 to 0.5 mole of dienophile are used per mole of the vitamin D resin being purified. The reaction with the dienophile can be carried out in the presence of any desired organic solvent which is inert under the reaction conditions, e.g. ether, toluene or heptane, or in the absence of a solvent. If it is intended to use a carrier, e.g. peanut oil, for the short-path distillation, it is advantageous to carry out the reaction with the dienophile in the presence of the carrier oil, since this reduces the high viscosity of vitamin D$_3$ resin and accordingly facilitates mixing of the reactants.

The reaction with the dienophile can be carried out at from 0° to 150° C., preferably from 20° to 80° C. Depending on the reactivity of the dienophile, a reaction time of from a few minutes to about 20 hours is required. Excess unreacted dienophile which still remains after the reaction is distilled off under from 0.001 to 1,000 mbar and at from 20° to 120° C.

The vitamin D which has been freed from excess dienophile is finally distilled over at from 130° to 200° C. and under from 0.001 to 0.1 mbar in a continuous short-path still in which the distance between the evaporation surface and the condensation surface should be no more than 5 cm. The short-path distillation can be carried out using a sparingly volatile carrier oil, for example a high-boiling paraffin or peanut oil. The temperature, the pressure and the feed are advantageously set so that from 70 to 95% of the vitamin distills over. Depending on the purity of the crude vitamin D resin used, the distillate contains from 65 to 78% of vitamin D. Thus, as a result of the novel process, the vitamin content is increased by 5–15% (absolute).

The bottom product of the short-path distillation can be recycled as many as five times. The total loss of desired product is then less than 3%.

EXAMPLE 1

0.4 g of p-benzoquinone and 19.3 g of vitamin $D_3$ resin, which contained 11.7% of provitamin $D_3$ and 49.0% of vitamin $D_3$, were dissolved in 100 ml of n-heptane. The solution was left to stand for 6 hours at 25° C., after which 19.3 g of peanut oil were added and the heptane was distilled off under 30 mbar, the bath temperature being increased to 80° C. The distillation residue was then metered continuously into a short-path still in the course of 84 minutes. The vitamin $D_3$ distilled over a distance of 1.3 cm from the evaporator surface to the condenser surface, distillation taking place at 150° C./0.01 mbar. 12.8 g of distillate containing 15.9% of provitamin $D_3$ and 57.1% of vitamin $D_3$ were obtained. The bottom product of the distillation comprised 26 g of an oil which contained 1.8% of provitamin $D_3$ and 7.0% of vitamin $D_3$.

EXAMPLE 2

1.6 g of p-benzoquinone and 85.4 g of vitamin $D_3$ resin, which contained 12.8% of provitamin $D_3$ and 51.4% of vitamin $D_3$, were mixed with 85.4 g of peanut oil at 60° C. The mixture was kept at 25° C. for 200 minutes and was then subjected to a continuous short-path distillation under the conditions described in Example 1. 69.8 g of distillate containing 13.7% of provitamin $D_3$ and 59.8% of vitamin $D_3$ were obtained. 101 g of bottom product, containing 0.5% of provitamin $D_3$ and 2.3% of vitamin $D_3$, resulted.

EXAMPLE 3

4.0 g of methyl acrylate and 50 g of vitamin $D_3$ resin, which contained 9.8% of provitamin $D_3$ and 50.4% of vitamin $D_3$, were mixed with 50 g of peanut oil at 60° C. The mixture was heated at 60° C. for 2 hours, after which traces of unreacted acrylate were evaporated at 80° C./30 mbar, and the remaining oil was then subjected to a continuous short-path distillation as described in Example 1. 32.1 g of distillate containing 11.7% of provitamin $D_3$ and 63.2% of vitamin $D_3$ were obtained. 71.0 g of bottom product, containing 1.8% of provitamin $D_3$ and 6.6% of vitamin $D_3$ resulted.

EXAMPLE 4

1.2 g of n-butyl acrylate and 19.9 g of vitamin $D_3$ resin, containing 7.2% of provitamin $D_3$ and 58.2% of vitamin $D_3$, were mixed with 19.9 g of peanut oil at 60° C. The mixture was heated at 50° C. for 2 hours after which traces of unreacted acrylate were evaporated at 80° C./30 mbar, and the remaining oil was then subjected to a continuous short-path distillation as described in Example 1. 15.0 g of distillate containing 10.8% of provitamin $D_3$ and 62.7% of vitamin $D_3$ were obtained. 25.5 g of bottom product, containing 2.0% of provitamin $D_3$ and 5.8% of vitamin $D_3$, resulted.

EXAMPLE 5

1.0 g of N-methylmaleimide and 20 g of vitamin $D_3$ resin, containing 11.9% of provitamin $D_3$ and 48.8% of vitamin $D_3$, were dissolved in 100 ml of methyl tert-butyl ether. The mixture was left to stand at 25° C. for 20 hours, after which 20 g of peanut oil were added and the solvent was distilled off under 30 mbar, the bath temperature being increased to 80° C. The remaining oil was then subjected to a continuous short-path distillation as described in Example 1. 16 g of distillate containing 9.7% of provitamin $D_3$ and 63.4% of vitamin $D_3$ were obtained. 25 g of distillation residue, containing 0.4% of provitamin $D_3$ and 1.2% of vitamin $D_3$, resulted.

EXAMPLE 6

1.6 g of N-phenylmaleimide and 20 g of vitamin $D_3$ resin, containing 11.9% of provitamin $D_3$ and 48.8% of vitamin $D_3$, were dissolved in 100 ml of methyl tert-butyl ether. Using the procedure described in Example 5, 15.5 g of distillate containing 10.2% of provitamin $D_3$ and 61.4% of vitamin $D_3$ were obtained. 26 g of distillation residue, containing 0.5% of provitamin $D_3$ and 3.3% of vitamin $D_3$, resulted.

EXAMPLE 7

4.8 g of methyl acrylate and 50 g of vitamin $D_2$ resin, containing 8.7% of provitamin $D_2$ and 54.2% of vitamin $D_2$, were dissolved in 50 g of peanut oil at 60° C. The mixture was heated at 60° C. for 2 hours, after which traces of unreacted acrylate were evaporated at 80° C./30 mbar, and the remaining oil was then subjected to a continuous short-path distillation as described in Example 1. 35.2 g of distillate containing 9.7% of provitamin $D_2$ and 88.1% of vitamin $D_2$ were obtained. 68 g of bottom product, containing 1.1% of provitamin $D_2$ and 4.8% of vitamin $D_2$, resulted.

EXAMPLE 8

60 g of methyl acrylate and 1,000 g of vitamin $D_3$ resin, containing 11.2% of provitamin $D_3$ and 52.4% of vitamin $D_3$, were mixed with 1,000 g of peanut oil at 60° C. The mixture was heated at 60° C. for 2 hours, after which traces of unreacted acrylate were evaporated at 80° C./30 mbar, and the remaining oil was then metered continuously into a short-path still in the course of 60 minutes. The vitamin $D_3$ distilled over a distance of 2.5 cm from the evaporator surface to the condenser surface, distillation taking place at 188° C./0.01 mbar. 768 g of distillate containing 11.8% of provitamin $D_3$ and 64.0% of vitamin $D_3$ were obtained. 1,282 g of distillation residue, containing 0.5% of provitamin $D_3$ and 3.7% of vitamin $D_3$, resulted.

The bottom product from the distillation was mixed with 1,282 g of vitamin $D_3$ resin, containing 11.2% of provitamin $D_3$ and 52.4% of vitamin $D_3$, and with 77 g of methyl acrylate at 60° C., and the resulting mixture was processed as described above. 1,090 g of distillate containing 9.9% of provitamin $D_3$ and 62.1% of vitamin $D_3$ were obtained. 1,540 g of bottom product, containing 0.8% of provitamin $D_3$ and 4.6% of vitamin $D_3$, were obtained.

The bottom product from the distillation was once again mixed with 1,540 g of vitamin $D_3$ resin, containing 11.2% of provitamin $D_3$ and 52.4% of vitamin $D_3$, and with 92 g of methyl acrylate at 60° C., and the resulting mixture was processed as described above. 1,335 g of distillate containing 10.1% of provitamin $D_3$ and 60.7% of vitamin $D_3$ were obtained. 1,820 g of bottom product, containing 0.7% of provitamin $D_3$ and 5.3% of vitamin $D_3$, resulted.

EXAMPLE 9

2.4 g of butanediol diacrylate and 36.3 g of vitamin $D_3$ resin, containing 11.2% of provitamin $D_3$ and 56.3% of vitamin $D_3$, were mixed with 36.3 g of peanut oil at 60° C. The mixture was heated at 60° C. for 4 hours, after which it was subjected to a continuous short-path distillation as described in Example 1. 29.2 g of distillate containing 16.7% of provitamin $D_3$ and 58.1% of vitamin $D_3$ were obtained. 45.6 g of distillation residue, containing 1.1% of provitamin $D_3$ and 4.8% of vitamin $D_3$, resulted.

EXAMPLE 10

1.8 g of acrylonitrile and 37.8 g of vitamin $D_3$ resin, containing 11.2% of provitamin $D_3$ and 56.3% of vitamin $D_3$, were mixed with 37.8 g of peanut oil at 60° C. The mixture was heated at 60° C. for 6 hours, after which traces of unreacted acrylonitrile were evaporated at 80° C./30 mbar, and the remaining oil was then subjected to a continuous short-path distillation as described in Example 1. 29.3 g of distillate containing 14.5% of provitamin $D_3$ and 59.4% of vitamin $D_3$ were obtained. 46.8 g of distillation residue, containing 1.2% of provitamin $D_3$ and 8.0% of vitamin $D_3$, resulted.

We claim:

1. A process for the purification of vitamin $D_3$, wherein vitamin $D_3$ resin is reacted with a dienophile, and the product is then subjected to a short-path distillation.

2. A process as claimed in claim 1, wherein vitamin $D_3$ resin is reacted with a dienophile which does not contain any strongly acidic groups or functional groups which can react with alcohol or water to form strongly acidic groups.

3. A process as claimed in claim 1, wherein the vitamin $D_3$ resin used has been obtained by irradiating 7-dehydrocholesterol or ergosterol.

4. A process as claimed in claim 1, wherein the reaction with the dienophile is carried out in a solvent.

5. A process as claimed in claim 1, wherein the vitamin $D_3$ resin is reacted with a dienophile which is substantially more volatile than vitamin $D_3$.

* * * * *